United States Patent [19]

Kristen et al.

[11] Patent Number: 4,889,938
[45] Date of Patent: Dec. 26, 1989

[54] 1,4-OXATHIANONES AND 1,4-OXATHIEPANONES

[75] Inventors: Ulrich Kristen, Riehen, Switzerland; Hermann O. Wirth, Bensheim, Fed. Rep. of Germany

[73] Assignee: Ciba-Geigy Corporation, Ardsley, N.Y.

[21] Appl. No.: 229,392

[22] Filed: Aug. 8, 1988

[30] Foreign Application Priority Data

Aug. 12, 1987 [CH]  Switzerland ............... 3097/87

[51] Int. Cl.⁴ ................... C07D 327/06; C07D 327/02
[52] U.S. Cl. ............................ 549/10; 549/14
[58] Field of Search ...................... 549/10, 14

[56] References Cited

U.S. PATENT DOCUMENTS 4,125,622 11/1978 Radunz et al. ............... 549/14

FOREIGN PATENT DOCUMENTS 0166696 1/1986 European Pat. Off. .
1165850 10/1969 United Kingdom .
1422360 1/1976 United Kingdom .

Primary Examiner—Alan L. Rotman
Assistant Examiner—MarySue Howard
Attorney, Agent, or Firm—JoAnn Villamizer

[57] ABSTRACT

The compounds of the formula

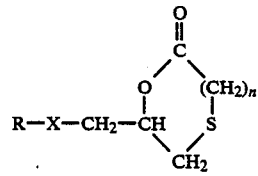

in which R is $C_1$-$C_{24}$alkyl, $C_3$-$C_{20}$alkenyl, $C_5$-$C_6$cycloalkyl, unsubstituted or $C_1$-$C_4$alkyl-substituted phenyl or phenyl-$C_1$-$C_4$alkyl, n is 1 or 2, and X is S or O, are highly suitable as additives, in particular as antiwear and high-pressure additives, and as corrosion inhibitors in functional fluids, for example in lubricants, fuels, hydraulic fluids, metal-working fluids and drilling fluids.

7 Claims, No Drawings

1,4-OXATHIANONES AND 1,4-OXATHIEPANONES

The present invention relates to substituted 1,4-oxathianones and 1,4-oxathiepanones, their use as additives for functional fluids, and compositions which contain such fluids and at least one of the compounds mentioned.

Lubricants and hydraulic fluids are generally admixed with various additives in order to improve their performance characteristics. Since lubricants require a high load-bearing capacity for transmission of relatively large forces, these so-called high-pressure and antiwear additives are added, whereby the wear phenomenon which otherwise occur are greatly reduced. On the other hand, if, for example, oxygen and moisture act simultaneously on a metal surface, corrosion can occur, which is why corrosion inhibitors are added with the object of preventing access of such substances to the metal surface. The oxidation reactions which occur in a lubricant to an increased extent, for example, at elevated temperature due to atmospheric oxygen can be suppressed by adding antioxidants. It is known that certain substances are able to combine a number of such properties as additives for lubricants; they are known as so-called multipurpose additives. Such substances are naturally in great demand for economic and practical reasons.

In practice, various phosphorus compounds are employed today as high-pressure and antiwear additives, in particular zinc dialkyldithiophosphates (ZDTP). Particularly in engine oils for petrol engines, the use of P-containing additives causes problems since they may reduce the efficiency of a catalytic converter for exhaust cleaning. There is therefore a demand for low-phosphorus or phosphorus-free oil additives.

A large number of such additives have already been proposed. For example, EP-A 166,696 describes products of the reaction of glycidyl thioethers with mercapto compounds which can be employed as high-pressure and antiwear additives.

Compounds have now been found which exhibit not only a good high-pressure and antiwear action, but can also be employed universally. In addition, they exhibit a good anticorrosion action. Moreover, their use is not limited to hydrophobic functional fluids. They can also be employed in aqueous or organic/aqueous systems.

The compounds according to the invention are those of the formula

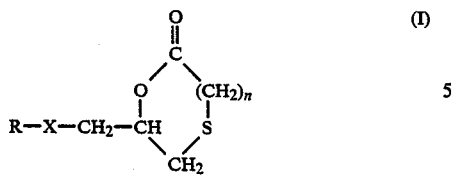

in which R is $C_1$–$C_{24}$alkyl, $C_2$–$C_{20}$alkenyl, $C_5$–$C_6$cycloalkyl, unsubstituted or $C_1$–$C_4$alkyl-substituted phenyl or phenyl-$C_1$–$C_4$alkyl, n is 1 or 2, and X is S or O.

The alkyl groups R preferably have 2–18, for example 2–16, in particular 4–18, for example 4–12 C atoms. Particularly preferred alkyl radicals are tertiary alkyl radicals, for example tert-butyl, tert-nonyl and tert-dodecyl. Substituted phenyl radicals may carry 1–3 alkyl groups, preferably 1 or 2, particularly methyl groups. Phenylalkyl is, in particular, phenethyl, α-methylbenzyl, α,α-dimethylbenzyl and particularly benzyl. Cycloalkyl is preferably cyclohexyl.

In the compounds of the formula I, n is preferably the number 1.

Compounds of the formula I which should be mentioned in particular are those in which R is $C_1$–$C_{18}$alkyl, $C_3$–$C_{18}$alkenyl, phenyl or benzyl, especially those in which R is $C_4$–$C_{18}$alkyl, phenyl or benzyl.

Of particular practical interest are those compounds of the formula I in which R is $C_4$–$C_{18}$alkyl, alkyl groups which contain at least one tertiary C atom being preferred.

Particularly preferred compounds of the formula (I) are those in which X is S.

The compounds of the formula I according to the invention can be prepared by processes which are known per se.

One possibility comprises intramolecular esterification (lactonization) of compounds of the formula

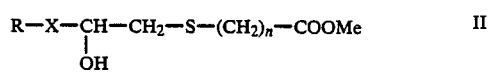

in which Me is the equivalent of an alkali metal ion or alkaline-earth metal ion, but in particular, Na, K or Li, especially Na, with the aid of acid catalysts. Acid catalysts which can be employed are organic or inorganic acids, for example a hydrohalic acid, oxo acids of sulfur or phosphorus, for example sulfuric acid, sulfonic acids (for example benzenesulfonic acid, p-toluenesulfonic acid), formic acid, acetic acid, etc. However, it is also possible to use acid ion exchangers. In particular, it is advantageous to use an acid ion exchanger to complete the reaction, even if acidification had previously been carried out using another acid.

The reaction may be illustrated by the equation

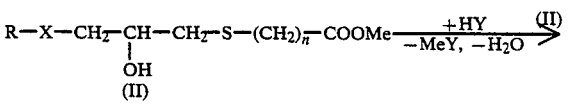

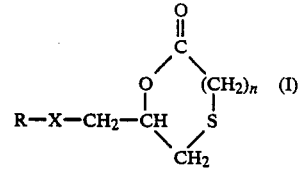

Y is, for example, Cl or ½$H_2SO_4$. The water formed can be removed by customary methods, for example with the aid of a rotary evaporator.

In principle, it is also possible to conduct the water separation using a suitable solvent, for example toluene, in an appropriate apparatus (azeotropic distillation using water separators). Here too, the reaction is carried out in the presence of an acid catalyst, for example p-toluene-sulfonic acid or, particularly expediently, an acid ion exchanger.

A further possibility comprises the intramolecular esterification of an ester derivative of the formula II with elimination of the alcohol according to the equation

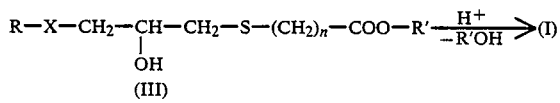

where R' is alkyl.

Suitable acid catalysts are again those mentioned above. The removal of the alcohol can take place analogously to the removal of the water in the first-mentioned method. Both processes can be carried out with or without solvent. The intramolecular esterification is preferably carried out directly in the reaction mixture in which the starting materials of the formulae II and III are prepared.

These starting materials can be obtained, for example, according to the equation

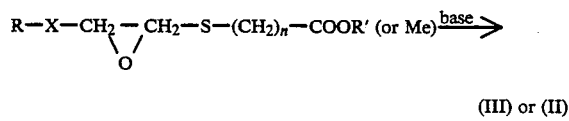

This reaction is carried out in the presence of a base, in particular at a pH of around 13 and preferably without additional solvent or in an aqueous medium. Details on the reaction as such and on preferred reaction parameters are revealed by EP-A 166,696. Particularly advantageous bases are tertiary amines such as tri($C_1$–$C_4$alkyl)amines and cyclic tertiary amines such as pyridine.

A further possibility for the preparation of the compounds of the formulae II and III is based on the following reaction:

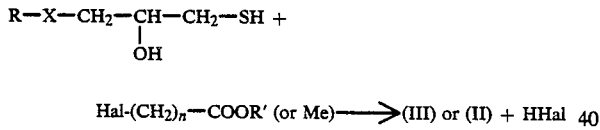

Hal is halogen, in particular Cl. The phase-transfer technique is advantageously used for this reaction. The HHal acceptor employed is expediently a base, for example NaOH. However, the reaction can also be carried out in a purely organic medium (solvent, for example toluene, dibutyl ether, etc.), the hydrogen halide acceptor used expediently being a tertiary amine.

The compounds of the formula I according to the invention have a liquid to viscous consistency. They are very readily soluble in nonpolar organic substances (for example in lubricating oils). However, they can also be introduced into polar systems (for example based on water and/or alcohols) and develop their action there, opening of the lactone ring taking place, at least in some cases. To this purpose, it may be advantageous to add small amounts of bases to aqueous systems of this type.

As a consequence of these properties, the compounds according to the invention can be used for an extremely wide range of applications in all types of functional fluids, whether based on nonpolar (for example oily) fluids or on (partially) polar (for example aqueous) systems. Examples which may be mentioned of functional fluids in which the compounds according to the invention can be employed are the following: lubricants, fuels, hydraulic fluids, metal-working fluids, cooling fluids and drilling fluids. The compounds exhibit very good stabilizer properties, in particular antiwear and high-pressure properties, but, in addition, have the advantage of a pronounced anticorrosion action.

Even in very small amounts, the compounds of the formula I are effective as additives in lubricants. They are expediently added to the lubricants in an amount from 0.01 to 5% by weight, preferably in an amount from 0.05 to 3% by weight, relative to the lubricant. The lubricants in question are known to those skilled in the art and described, for example, in "Schmierstoffe und verwandte Produkte" [Lubricants and Related Products] (Verlag Chemie, Weinheim, 1982). Poly-α-olefins, lubricants based on esters, phosphates, glycols, polyglycols and polyalkylene glycols, for example, are particularly suitable in addition to mineral oils.

In addition, lubricants may contain other additives which are added in order to further improve the basic properties of lubricants; these include: antioxidants, metal passivators, rust inhibitors, viscosity index improvers, pour-point reducers, dispersants, detergents, and further high-pressure additives and antiwear additives. Some examples of additional additives of this type are listed below:

EXAMPLES OF PHENOLIC ANTIOXIDANTS

1. Alkylated monophenols 2,6-Di-tert-butyl-4-methylphenol
2,6-Di-tert-butylphenol
2-tert-Butyl-4,6-dimethylphenol
2,6-Di-tert-butyl-4-ethylphenol
2,6-Di-tert-butyl-4-n-butylphenol
2,6-Di-tert-butyl-4-iso-butylphenol
2,6-Di-cyclopentyl-4-methylphenol
2-(α-Methylcyclohexyl)-4,6-dimethylphenol
2,6-Di-octadecyl-4-methylphenol
2,4,6-Tri-cyclohexylphenol
2,6-Di-tert-butyl-4-methoxymethylphenol
o-tert-Butylphenol 2. Alkylated hydroquinones 2,6-Di-tert-butyl-4-methoxyphenol
2,5-Di-tert-butyl-hydroquinone
2,5-Di-tert-amyl-hydroquinone
2,6-Diphenyl-4-octadecyloxyphenol 3. Hydroxylated diphenyl thioethers 2,2'-Thio-bis-(6-tert-butyl-4-methyphenol)
2,2'-Thio-bis-(4-octylphenol)
4,4'-Thio-bis-(6-tert-butyl-3-methyphenol)
4,4'-Thio-bis-(6-tert-butyl-2-methyphenol)

4. Alkylidene-bisphenols 2,2'-Methylene-bis-(6-tert-butyl-4-methylphenol)
2,2'-Methylene-bis-(6-tert-butyl-4-ethylphenol)
2,2'-Methylene-bis-[4-methyl-6-(α-methylcyclohexyl)-phenol]
2,2'-Methylene-bis-(4-methyl-6-cyclohexylphenol)
2,2'-Methylene-bis-(6-nonyl-4-methylphenol)
2,2'-Methylene-bis-(4,6-di-tert-butylphenol)
2,2'-Ethylidene-bis-(4,6-di-tert-butylphenol)
2,2'-Ethylidene-bis-(6-tert-butyl-4-iso-butylphenol)
2,2'-Methylene-bis-[6-(α-methylbenzyl)-4-nonylphenol]
2,2'-Methylene-bis-[6-(α-dimethylbenzyl)-4-nonylphenol]
4,4'-Methylene-bis-(2,6-di-tert-butylphenol)
4,4'-Methylene-bis-(6-tert-butyl-2-methylphenol)
1,1-Bis-(5-tert-butyl-4-hydroxy-2-methylphenyl)-butane 2,6-Di-(3-tert-butyl-5-methyl-2-hydroxybenzyl)-4-methylphenol
1,1,3-Tris-(5-tert-butyl-4-hydroxy-2-methylphenyl)-3-n-dodecylmercaptobutane
Ethylene glycol bis-[3,3-bis-(3'-tert-butyl-4'-hydroxyphenyl)-butyrate]
Di-(3-tert-butyl-4-hydroxy-5-methylphenyl)-dicyclopentadiene
Di-[2-(3'-tert-butyl-2'-hydroxy-5'-methyl-benzyl)-6-tert-butyl-4-methylphenyl] terephthalate.

5. Benzyl compounds 1,3,5-Tri-(3,5-di-tert-butyl-4-hydroxybenzyl)-2,4,6-trimethylbenzene
Di-(3,5-di-tert-butyl-4-hydroxybenzyl) sulfide
Isooctyl 3,5-di-tert-butyl-4-hydroxybenzyl-mercaptoacetate
Bis-(4-tert-butyl-3-hydroxy-2,6-dimethylbenzyl)-dithiol terephthalate
1,3,5-Tris-(3,5-di-tert-butyl-4-hydroxybenzyl) isocyanurate
1,3,5-Tris-(4-tert-butyl-3-hydroxy-2,6-dimethylbenzyl)-isocyanurate
Dioctadecyl 3,5-di-tert-butyl-4-hydroxybenzyl-phosphonate
Monoethyl 3,5-di-tert-butyl-4-hydroxybenzyl-phosphonate, calcium salt.

6. Acylaminophenols

4-Hydroxy-lauranilide
4-Hydroxy-stearanilide
2,4-Bis-octylmercapto-6-(3,5-di-tert-butyl-4-hydroxyanilino)-s-triazine
Octyl N-(3,5-di-tert-butyl-4-hydroxyphenyl)-carbamate.

7. Esters of β-(3,5-di-tert-butyl-4-hydroxyphenyl)-propionic acid with monohydric or polyhydric alcohols, for example with

| | |
|---|---|
| Methanol | Diethylene glycol |
| Octadecanol | Triethylene glycol |
| 1,6-Hexanediol | Pentaerythritol |
| Neopentyl glycol | Tris-hydroxyethyl isocyanurate |
| Thiodiethylene glycol | Di-hydroxyethyl-oxalic diamide |

8. Esters of β-(5-tert-butyl-4-hydroxy-3-methylphenyl)-propionic acid with monohydric or polyhydric alcohols, for example with

| | |
|---|---|
| Methanol | Diethylene glycol |
| Octadecanol | Triethylene glycol |
| 1,6-Hexanediol | Pentaerythritol |
| Neopentyl glycol | Tris-hydroxyethyl isocyanurate |
| Thiodiethylene glycol | Di-hydroxyethyl-oxalic diamide |

9. Amides of β-(3,5-di-tert-butyl-4-hydroxyphenyl)-propionic acid for example
N,N'-Di-(3,5-di-tert-butyl-4-hydroxyphenylpropionyl)-hexamethylenediamine
N,N'-Di-(3,5-di-tert-butyl-4-hydroxyphenylpropionyl)-trimethylenediamine
N,N'-Di-(3,5-di-tert-butyl-4-hydroxyphenylpropionyl)-hydrazine.

Examples of aminic antioxidants:
N,N'-Di-isopropyl-p-phenylenediamine
N,N'-Di-sec-butyl-p-phenylenediamine
N,N'-Bis(1,4-dimethyl-pentyl)-p-phenylenediamine
N,N'-Bis(1-ethyl-3-methyl-pentyl)-p-phenylenediamine
N,N'-Bis(1-methyl-heptyl)-p-phenylenediamine
N,N'-Diphenyl-p-phenylenediamine
N,N'-Di-(naphth-2-yl)-p-phenylenediamine
N-Isopropyl-N'-phenyl-p-phenylenediamine
N-(1,3-Dimethyl-butyl)-N'-phenyl-p-phenylenediamine
N-(1-Methyl-heptyl)-N'-phenyl-p-phenylenediamine
N-Cyclohexyl-N'-phenyl-p-phenylenediamine
4-(p-Toluene-sulfonamido)-diphenylamine
N,N'-Dimethyl-N,N'-di-sec-butyl-p-phenylenediamine
Diphenylamine
4-Isopropoxy-diphenylamine
N-Phenyl-1-naphthylamine
N-Phenyl-2-naphthylamine
Octylated diphenylamine
4-n-Butylaminophenol
4-Butyrylamino-phenol
4-Nonanoylamino-phenol
4-Dodecanoylamino-phenol
4-Octadecanoylamino-phenol
Di-(4-methoxy-phenyl)-amine
2,6-Di-tert-butyl-4-dimethylamino-methyl-phenol
2,4'-Diamino-diphenylmethane
4,4-Diamino-diphenylmethane
N,N,N',N'-Tetramethyl-4,4'-diamino-diphenylmethane
1,2-Di-[(2-methyl-phenyl)-amino]-ethane
1,2-Di-(phenylamino)-propane
(o-Tolyl) biguanide
Di-[4-(1',3'-dimethyl-butyl)-phenyl]amine
Tert-octylated N-phenyl-1-naphthylamine
Mixtures of monoalkylated and dialkylated tert-butyl-/tert-octyldiphenylamines.

Examples of metal passivators are:
for copper, for example:
triazole, benzotriazole and derivatives thereof, 2-mercaptobenzothiazole, 2,5-dimercaptothiadiazole, salicylidene-propylenediamine, salts of salicylaminoguanidine.

Examples of rust inhibitors are:
(a) Organic acids, their esters, metal salts and anhydrides, for example: N-oleoyl-sarcosine, sorbitan monooleate, lead naphthenate, dodecenylsuccinic anhydride, alkenylsuccinic semiesters, 4-nonylphenoxy-acetic acid.
(b) Nitrogen-containing compounds, for example:
 I. Primary, secondary or tertiary aliphatic or cycloaliphatic amines and amine salts of organic and inorganic acids, for example oil-soluble alkylammonium carboxylates.
 II. Heterocyclic compounds, for example: substituted imidazolines and oxazolines.
(c) Phosphorus-containing compounds, for example: amine salts of partial esters of phosphoric acid.
(d) Sulfur-containing compounds, for example: barium dinonylnaphthalenesulfonates, calcium petroleum sulfonates.

Examples of viscosity improvers are, for example:
polymethacrylates, vinylpyrrolidone/methacrylate copolymers, polybutenes, olefin copolymers, styrene/acrylate copolymers.

Examples of pour-point reducers are, for example:
polymethacrylate, alkylated naphthalene derivatives.

Examples of dispersants/surfactants are, for example:
polybutenylsuccinimides, polybutenylphosphonic acid derivatives, basic magnesium, calcium and barium sulfonates and phenoxides.

Examples of antiwear agents are, for example:
compounds containing sulfur and/or phosphorus and/or halogen, such as sulfurized vegetable oils, zinc dialkyldithiophosphates, tritolyl phosphate, chlorinated paraffins, alkyl and aryl disulfides.

The compounds according to the invention are used, in particular, as additives for lubricant systems, in particular engine oils. They have high-pressure, antiwear, antioxidant and corrosion-inhibition actions in lubricant systems. A particular advantage of these compounds is that they are free of phosphorus and tin, in contrast to compounds having comparable properties, which also means that post-combustion of the exhaust gases is not impaired.

However, the compounds of the formula I according to the invention are, as already stated, also very good high-pressure and antiwear additives for polar functional fluids. In addition, they also act as anticorrosion agents.

The compounds of the formula I can also be employed in the homogeneous solution state in polar functional fluids, in particular based on water, ethylene glycol, diethylene glycol, polyethylene glycol and blends thereof with water. They can also be employed in functional fluids based on phosphoric acid esters, preferably aryl phosphates. However, colloidal systems are also very valuable industrially, in particular due to their favourable dispersion and emulsion properties, for example for the production of emulsions and microemulsions.

The compounds of the formula I can also be employed, especially, in polar functional fluids with a complex structure containing water as the predominant base fluid, in particular having a water content of at least 50% by weight and optionally having a content of low-molecular-weight glycol compounds, for example ethylene glycol, diethylene glycol or thiodiethylene glycol, and furthermore containing, as further components, phosphoric acid and a base in order to adjust the pH to a value between 7.5 and 12, preferably 8.5.

Bases for pH regulation are, for example, alkali metal hydroxides, preferably potassium hydroxide, and water-soluble organic bases, preferably alkanolamines, in particular ethanolamine. It is also possible to employ polymeric amines, for example polyethyleneimine, for the pH regulation.

The above functional fluid with a complex structure can also contain, as further components, fatty acids, preferably oleic acid, and, if desired, also boric acid.

The polar functional fluids with a complex structure may also contain additional additives which are added in order to further improve the basic properties of these functional fluids; these include: further anticorrosion agents, defoamers, softeners and biocides.

Examples of corrosion inhibitors are the following:

(a) organic acids, their esters, ammonium, amine, alkanolamine and metal salts, for example benzoic acid, p-tert-butyl-benzoic acid, di-Na sebacate, triethanolamine laurate, isononanoic acid, the triethanolamine salt of p-toluenesulfonamidocaproic acid, the triethanolamine salt of benzenesulfonamidocaproic acid, triethanolamine salts of 5-ketocarboxylic acid derivatives, as described in EP-A 41,927, sodium N-lauroyl-sarcosinate or nonylphenoxyacetic acid.

(b) Nitrogen-containing substances, for example fatty acid alkanolamides, imidazolines, for example 1-hydroxy-ethyl-2-oleyl-imidazoline, oxazolines, triazoles, for example benzotriazoles, or the Mannich base derivatives thereof, triethanolamines, fatty amines, inorganic salts, for example sodium nitrate, and the carboxytriazine compounds described in EP-A 46,139.

(c) Phosphorus-containing substances, for example amine phosphates, phosphonic acids or inorganic salts, for example Na dihydrogen phosphate or zinc phosphate.

(d) Sulfur-containing compounds, for example sodium, calcium or barium petroleumsulfonates or heterocyclic compounds, for example Na mercaptobenzothiazole.

Complexing agents, such as nitrilotriacetic acid and salts thereof, defoaming agents, such as silicones, for example polydimethylsiloxanes, distearyl sebacamide, distearyl adipamide and similar products derived from ethylene oxide and/or propylene oxide condensations, addition products of fatty alcohols, such as caprylic alcohols, and products of the condensation thereof with ethylene oxide, furthermore biocides, for example amines, quaternary ammonium compounds, chlorophenols, sulfur-containing compounds, such as sulfones, methylene bis-thiocyanates, methylene carbamates, isothiazolones, bromopropionamides, triazines, phosphonium compounds, chlorine and chlorine-releasing substances and organometallic compounds, such as tributyltin oxide, can also be additionally employed.

The concomitant use of an additional thickener as a further component is advantageous for the use of compounds of the formula I in hydraulic fluids.

Suitable thickeners are, for example, polyalkylene oxides, polyalkyl methacrylates, polyamide esters, polyamide alkoxylates or polyethyleneimines, which can at the same time take on the function of a pH regulator in full or in part.

The amount of thickener employed is expediently between 2 and 50% by weight, preferably between 5 and 15% by weight, relative to the base fluid.

The amount of the compounds of the formula I employed is, for example, 0.01 to 10% by weight, preferably 0.01 to 5% by weight, for example 0.05 to 3% by weight, relative to the total amount of the polar functional fluid.

If the compounds of the formula I are employed in functional fluids having a complex structure, the amount of them used is, in particular, 0.5-2% by weight, but preferably 0.5-1% by weight, relative to the total amount of the functional fluid with a complex structure, the total amount of the additives added preferably making up 0.5 to 10% by weight, in particular 2.5-5% by weight, relative to their water content.

Polar functional fluids, in particular those based on water, ethylene glycol, diethylene glycol, polyethylene glycol and blends thereof with water or based on phosphoric acid esters, and functional fluids having a complex structure can be employed, for example, as hydraulic fluids, metal-working fluids, cooling fluids or as drilling fluids, in particular as hydraulic fluids.

As a consequence of the abovementioned possible uses for the compounds of the formula I according to the invention, the invention also relates to compositions which contain a functional fluid and at least one compound of the formula I. In these compositions, the functional fluid is, in particular, a lubricant (for example an engine oil), a fuel, a hydraulic fluid, a metal-working fluid, a cooling fluid or a drilling fluid. Examples of the type and composition of such fluids are given above. In particular, compositions should be mentioned which contain a natural (for example based on mineral oil) or synthetic lubricant oil or a hydraulic fluid and at least one compound of the formula I.

The amount of the compound of the formula I in the compositions according to the invention is preferably 0.01–5% by weight, in particular 0.05 to 3% by weight, relative to the functional fluid.

The examples below illustrate the invention in greater detail. In these examples, as in the remainder of the description and in the patent claims, the percentages and parts are by weight, unless otherwise stated.

EXAMPLE 1

An aqueous solution, adjusted to pH 13 using dilute sodium hydroxide solution, of 0.5 mol of sodium thioglycolate [to be prepared from 46 g (0.5 mol) of thioglycolic acid and 40.6 g (0.5 mol) of sodium hydroxide in 200 ml of water] is treated with stirring at about 50° C. with 108 g (0.5 mol) of tert-nonyl glycidyl thioether at a rate such that this temperature is maintained. After the addition has ended, the mixture is warmed at about 60° C. for a further 30 minutes.

After cooling, the reaction mixture, which has partly deposited in crystalline form, is treated with 70 ml of concentrated hydrochloric acid, and two liquid phases form. The upper organic phase is separated off and treated with about 5 g of an acid ion exchanger (®Lewatit 1080) in order to complete the esterification reaction.

After removing the ion exchanger, 285.5 g of the compound of the formula

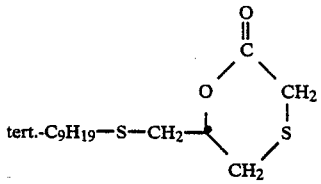

are obtained as a pale yellow liquid having a $n_D^{20}$ of 1.5222.

EXAMPLE 2

53 g (0.5 mol) of methyl thioglycolate are introduced into a 250 ml three-neck flask equipped with stirrer, reflux condenser and thermometer, 2 ml of triethylamine are added, and the mixture is then warmed to about 60° C. 73 g (0.5 mol) of tert-butyl glycidyl thioether are subsequently added dropwise. After the addition has ended, the mixture is warmed to 80° C. for about 1 further hour, until glycidyl thioether can no longer be detected in the TLC test.

The triethylamine is removed from the reaction mixture by briefly applying a vacuum. About 10 g of an acidified ion exchanger (®Lewatit 1080) are subsequently added, and the methanol formed during the lactone formation is then removed by distillation over a short column, the temperature of the reaction mixture being increased gradually to about 120° C.

After the reaction mixture has been cooled, the ion exchanger is filtered off and the volatile components remaining are removed in vacuo by means of a rotary evaporator. 125 g of the compound of the formula

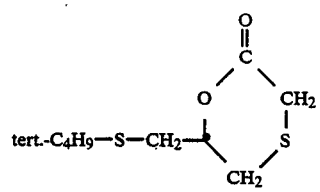

are obtained as the residue as a pale yellow liquid.

After distillation at 148°–150° C. at a presure of 0.25 torr, the compound crystallizes. Melting point: 73° C.

EXAMPLE 3

96.2 g of the compound of the formula tert-$C_4H_9$—S—$CH_2CH(OH)$—$CH_2$—S—$CH_2$—COOH, 4 g of an acid ion exchanger (®Lewatit S 1080) and 250 ml of toluene are introduced into a 500 ml three-neck flask equipped with reflux condenser, thermometer, water separator and stirrer, and the reaction mixture is heated at the reflux temperature while stirring for 140 minutes, the water of reaction formed (7.2 ml) being removed via the water separator. After addition of a further 2 g of the ion exchanger, a further 1.2 ml of water are removed at the reflux temperature. The ion exchanger is then removed using a fluted filter, and the solvent is removed on a rotary evaporator. After distillation of the residue at 148°–150° C. and 0.25 torr, 53.3 g of the same compound as in Example 2 having a melting point of 72°–73° C. are obtained.

EXAMPLE 4

22 g of NaOH are dissolved in 300 ml of water in a 1 l four-neck flask equipped with stirrer, dropping funnel, thermometer and reflux condenser, 46.1 g of α-mercaptoacetic acid are added dropwise, and 73.1 g of tert-butyl glycidyl thioether are subsequently added at 60°–70° C. over the course of 30 minutes (exothermic reaction). The mixture is left to stand overnight, and 72.9 g of 32% HCl are then added dropwise, and the aqueous phase is separated off and washed once with diethyl ether. The combined organic phases are washed with 100 ml of water, dried and evaporated to a residue. 98.6 g of a pale yellow liquid having $n_D^{20}$ of 1.5330 are thus obtained. The product corresponds to that obtained in Example 2 and can likewise be further purified by distillation.

EXAMPLE 5

The following values were determined using the Shell four-ball machine (IP 239/73 extreme pressure and wear lubricant test for oils and greases—four-ball machine):

1. W.L.=Weld load. This is the load at which the 4 balls weld together within 10 seconds.
2. W.S.D.=Wear scar diameter in mm: this is the mean wear diameter at a load of 400N for 10 minutes.

The fluid used to test the effectiveness of the additives is a base oil of viscosity ISO-VH 100 having a low aromatics content and containing 0.035% of S. The concentration of the additives in the oil is 1%.

The results are collated in Table 1 below.

TABLE 1

| Additive according to Example No. | W.L. (N) 1% of additive | W.S.D. (mm) 1% of additive |
|---|---|---|
| none | 1,450 | 0.95 |
| 1 | 2,000 | 0.70 |

EXAMPLE 6

FZG test for EP/AW properties in accordance with *DIN* 51354. FZG=Forschungsstelle Zahnräder und Getriebe [Research Centre for Gear Wheels and Gear Boxes], TU Munich.

The performance of the test in accordance with the standard mentioned can be described briefly as follows: defined gear wheels run in the lubricant under test in a dip lubrication system at a constant speed and a fixed initial oil temperature. The load on the tooth flanks is increased in stages (load stages 1 to 12). From load stage 4, the change in the tooth flanks is recorded at the end of each load stage by description, roughness measurement or contrast impressions. As a measure of the effectiveness of the lubricant oil, the load stage is determined at which the sum of the damage to the teeth of the pinion (widths of all scores and seizure lines of the tooth flanks) is more than 20 mm. This load stage is known as the failure load stage (FLS). The higher the failure load stage, the more effective the lubricant oil tested.

In the present example, the base oil used is a mineral oil VG 32. In order to test the effectiveness as an additive, 0.4% of the compound of Example 1 is added to this base oil. The test results obtained can be seen from Table 2 below.

TABLE 2

| Additive from | FLS |
|---|---|
| — | 5 |
| Example 1 (0.4%) | 12 |

What is claimed is:
1. A compound of the formula

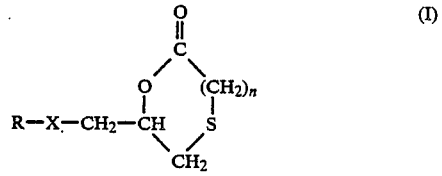

in which R is $C_1$-$C_{24}$alkyl, $C_3$-$C_{20}$alkenyl, $C_5$-$C_6$cycloalkyl, unsubstituted or $C_1$-$C_4$alkyl-substituted phenyl or phenyl-$C_1$-$C_4$alkyl, n is 1 or 2, X is O or S.

2. A compound according to claim 1, in which n is 1.
3. A compound according to claim 1, in which R is $C_1$-$C_{18}$alkyl, $C_3$-$C_{18}$alkenyl, phenyl or benzyl.
4. A compound according to claim 3, in which R is $C_4$-$C_{18}$alkyl, phenyl or benzyl.
5. A compound according to claim 1, in which the alkyl group R contains at least one tertiary C atom.
6. A compound according to claim 4, in which R is $C_4$-$C_{18}$alkyl.
7. A compound according to claim 1, in which X is S.

* * * * *